US00PP10237P

United States Patent [19]

Neeman

[11] Patent Number: Plant 10,237

[45] Date of Patent: Feb. 10, 1998

[54] NEW GUINEA IMPATIENS PLANT NAMED 'VOLCANO DEEP RED'

[75] Inventor: Lior Neeman, Netaim D.N. Emek Sorek, Israel

[73] Assignee: Milestone Agriculture Inc., Apopka, Fla.

[21] Appl. No.: 699,577

[22] Filed: Aug. 19, 1996

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,263 6/1993 Dehan ..... Plt./87.6
P.P. 8,401 9/1993 Kientzler ..... Plt./87.6

*Primary Examiner*—James R. Feyrer
*Assistant Examiner*—Kent L. Bell
*Attorney, Agent, or Firm*—C. A. Whealy

[57] ABSTRACT

A new and distinct cultivar of New Guinea Impatiens plant named 'Volcano Deep Red', characterized by its dark hot pink and red flowers; vigorous growth habit; dark reddish green, glossy, non-variegated foliage; and freely branching plant habit.

1 Drawing Sheet

The present invention relates to a new and distinct cultivar of New Guinea Impatiens plant, botanically known as *Impatiens hawkeri*, and hereinafter referred to by the cultivar name 'Volcano Deep Red'.

The new cultivar is a product of a planned breeding program conducted by the inventor in Paraiso, Costa Rica. The objective of the breeding program was to develop new varieties that are freely branching, uniform in plant habit, and have bright flower colors.

The new cultivar originated from a cross made by the inventor in January, 1994, of two unnamed proprietary seedlings. The cultivar 'Volcano Deep Red' was discovered and selected by the inventor as a flowering plant within the progeny of the stated cross in a controlled environment in Paraiso, Costa Rica. Asexual reproduction of the new cultivar by terminal cuttings taken at Paraiso, Costa Rica, has shown that the unique features of this new Impatiens are stable and reproduced true to type in successive generations of asexual reproduction.

The following traits have been repeatedly observed and are determined to be the unique characteristics of 'Volcano Deep Red'. These characeristics in combination distinguish 'Volcano Deep Red' as a new and distinct cultivar:

1. Dark hot pink and red flowers.
2. Vigorous growth habit.
3. Dark reddish green, glossy, non-variegated foliage.
4. Freely branching plant habit.

The new Impatiens is similar in flower color to the cultivar 'Danhill', disclosed in U.S. Plant Pat. No. 8,263. However in side-by-side comparisions conducted in Apopka, Fla., plants of the new Impatiens had larger leaves and darker foliage than plants of the cultivar 'Danhill'. The new Impatiens is also similar to the cultivar 'Marpesia', disclosed in U.S. Plant Pat. No. 8,401. However in side-by-side comparisons conducted in Apopka, Fla., plants of the new Impatiens had darker foliage and flowers were more red in color than plants of the cultivar 'Marpesia'.

The accompaning colored photograph illustrates the overall appearance of the new cultivar, showing the colors as true as it is reasonably possible to obtain in colored reproductions of this type. The photograph comprises a top perspective view of a typical plant of 'Volcano Deep Red'. The flower and foliage color in the photographs may differ from the actual colors due to light reflectance.

The cultivar 'Volcano Deep Red' has not been observed under all possible environmental conditions. The phenotype may vary somewhat with variations in environment such as temperature and light intensity, without, however, any variance in genotype. The following observations, measurements and comparisons describe plants grown in Apopka, Fla., under commercial practice in a polyethylene-covered greenhouse in 25-cm containers with five plants per container.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens.

*Cultivar.*—'Volcano Deep Red'.

Parentage:

*Male parent.*—Unnamed proprietary seedling.

*Female parent.*—Unnamed proprietary seedling.

Propagation:

*Type cutting.*—Terminal cuttings.

*Time to initiate roots.*—About 7 days with 21° C. soil temperature.

Plant description:

*General appearance.*—Rounded and dense plant form; freely branching; upright and vigorous growth habit.

*Plant height.*—About 30 cm from soil level to top of plant plane.

*Foliage description.*—Shape: Elliptic with acuminate tip and attenuate base. Size: Length: About 11 cm. Width: About 4 cm. Texture: Smooth, glossy, and glabrous. Margin: Finely serrated, ciliate. Petiole length: About 3.5 cm. Color: Young foliage, abaxial surface: 147A. Young foliage, adaxial surface: 183A. Mature foliage, abaxial surface: Darker than 147A with reddish overtones. Mature foliage, adaxial surface: 183A. Veins, abaxial and adaxial surfaces: 59A. Petiole: 59A.

*Stem description.*—Internode length: About 5.5 cm. Stem color: Mature: 144A. Immature: 59A.

Flower description:

*Flowering habit.*—Freely flowering.

*Natural flowering season.*—Year-round. Plants usually flower 7 to 8 weeks after planting.

*Flowers borne.*—Flower buds develop in apical leaf axils. Open flowers are displayed above the foliage.

*Quantity of flowers.*—Usually 5 to 8 flower buds and open flowers per terminal.

*Flower longevity on plant.*—From opening, flowers last about 7 days.

*Flower height.*—About 4.5 cm.

*Flower width.*—About 5 cm.

*Flower depth.*—About 7.5 mm.

*Petals.*—Shape: Cordate. Quantity, arrangement: 5 petals overlapping. Aspect: Cupped. Size: Length: Uppermost petal: About 2 cm. Lower Petals: About 2.5 cm Width: Uppermost petal: About 2.5 cm. Lower petals: About 2 cm. Texture: Smooth, satiny, and glabrous. Margin: Entire. Color: Abadial surface: Iridescent; background, 57A; midribs, center and base, redder than 46B. Adaxial surface: 47C.

*Peduncle.*—Angle: Erect. Length: About 3.5 cm. Color: Proximal: 144A. Distal: 47A.

*Flower bud.*—Shape: Ovoid with spur. Length: About 1.5 cm. Diameter: About 1 cm. Color: Abaxial side: 46A. Lateral and adaxial sides: 47B.

*Spur.*—Shape: Needle-shaped, curved at end. Color: Flower bud: 53A. Opened flower: 53A.

*Sepals.*—Arrangement: Opposite. Quantity: 2. Shape: Ensiform with acuminate tip. Texture: Shiny, smooth and glabrous. Margin: Entire. Color: Abaxial side: 46A. Adaxial side: Light green with reddish overtones.

*Reproductive organs.*—Androecium: Quantity of stamens: 5. Anther color: 57A. Pollen color: 11D. Gynoecium: Ovary color: 59A.

Disease resistance: Under commercial conditions, no fungal, bacterial nor viral problems observed.

Seed development: Seed production is not usually observed.

It is claimed:

1. A new and distinct cultivar of New Guinea Impatiens plant named 'Volcano Deep Red', as illustrated and described.

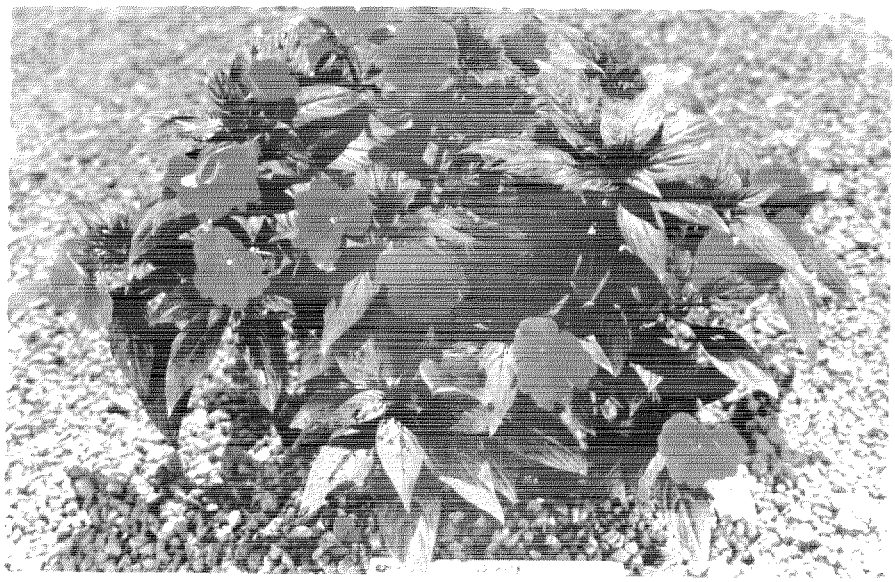

* * * * *